(12) United States Patent
Schickli et al.

(10) Patent No.: US 11,883,267 B2
(45) Date of Patent: Jan. 30, 2024

(54) TAMPON AND METHOD FOR MAKING SAME

(71) Applicant: The Procter & Gamble Company, Cincinnati, OH (US)

(72) Inventors: Eric Mitchell Schickli, Cincinnati, OH (US); Eva Grace Nellenbach, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 269 days.

(21) Appl. No.: 14/136,099

(22) Filed: Dec. 20, 2013

(65) Prior Publication Data

US 2015/0173966 A1 Jun. 25, 2015

(51) Int. Cl.
*A61F 13/20* (2006.01)

(52) U.S. Cl.
CPC ...... *A61F 13/2054* (2013.01); *A61F 13/2082* (2013.01); *A61F 13/2085* (2013.01); *A61F 13/2088* (2013.01)

(58) Field of Classification Search
CPC .............. A61F 13/2051; A61F 13/2054; A61F 13/2065; A61F 13/36; A61F 13/2082; A61F 13/2085; A61F 13/2088
USPC ................................ 604/385.17, 385.18, 904
See application file for complete search history.

(56) References Cited

U.S. PATENT DOCUMENTS

| | | | |
|---|---|---|---|
| 5,659,934 A | 8/1997 | Jessup et al. | |
| 6,554,814 B1 | 4/2003 | Agyapong et al. | |
| 6,837,882 B2 | 1/2005 | Agyapong et al. | |
| 7,992,270 B2 | 8/2011 | Gilbert | |
| 2003/0208180 A1 | 11/2003 | Fuchs et al. | |
| 2004/0193131 A1 | 9/2004 | Wada | |
| 2008/0026246 A1 | 1/2008 | Saga et al. | |
| 2008/0262464 A1 | 10/2008 | Hasse et al. | |
| 2010/0268182 A1 | 10/2010 | Edgett et al. | |

FOREIGN PATENT DOCUMENTS

GB 1387915 A 3/1975

OTHER PUBLICATIONS

US 6,353,147 B1, 03/2002, Foley et al. (withdrawn)
PCT International Search Report, dated Mar. 11, 2015, 81 pages.
13185 EP Search Report and Written Opinion for PCT/US14/70257 dated Mar. 2, 2018.
13185 Third Party Opposition for 14825529.2 dated Nov. 12, 2019, 1 pages.
Code of federal Regulations Title 21, Year 1996, 668 Pages.
Dictionary Of Fiber Textile Technology (Amyuni).pdf, Year: Unknown, pp. 228.
Hannah, Andrea, "The 5 Best Tampons For Beginners", Mar. 30, 2019, [cited Dec. 15, 2020] Available from: [https://www.elitedaily.com/p/the-5-best-tampons-for-beginners-16824291], 06 Pages.
Presentation: Rayon Fibers; The Versatile Choice for Wipes, Dec. 2008, 47 Pages.
Yang Sarah, "These Are the Best Tampons for a HeavyFlow" Aug. 5, 2019, [cited Dec. 15, 2020] Available from [https://thethirty.whowhatwear.com/best-tampons-for-a-heavy flow, 09 Pages.

*Primary Examiner* — Jacqueline F Stephens
(74) *Attorney, Agent, or Firm* — Sarah M. DeCristofaro; Andrew J. Hagerty

(57) ABSTRACT

Tampons that provide a balance of adequate absorption with sufficient expansion properties during absorption and a relatively small initial diameter for comfortable insertion are provided.

17 Claims, 5 Drawing Sheets

TAMPON AND METHOD FOR MAKING SAME

FIELD

The present disclosure relates to tampons and methods for making tampons.

BACKGROUND

The size of a tampon can negatively affect insertion comfort. And some consumers may compromise protection in favor of insertion comfort by selecting a lower absorbency tampon than may be needed where the consumer is anxious about tampon insertion or concerned about discomfort associated with tampon insertion. This can be particularly true for first time users of tampons, users during days of relatively light flow, as well as aging consumers that have decreased vaginal moisture levels.

Some tampon manufacturers offer smaller diameter tampons to address insertion comfort concerns. These tampons are generally compressed to a higher density level to achieve the smaller size. And while the tampons may ultimately absorb a certain capacity, the highly compressed tampons due to design and manufacturing properties can be slow to expand and/or expand to a limited overall amount, both of which can lead to by-pass leakage.

What is needed is a tampon that provides a balance of adequate absorption with sufficient expansion prior to full absorption, and that has a relatively small initial diameter for comfortable insertion. Tampons of the present invention address this need.

SUMMARY

The present disclosure relates to tampons having different absorbent capacities and other properties. In accordance with one exemplary embodiment, there has now been provided a tampon comprising a mass of absorbent material which has been compressed into a generally cylindrical, self-sustaining form. The tampon has a syngyna absorbent capacity of between about 6 and about 9 grams. Subsequent to compression, the generally cylindrical, self-sustaining form comprises a maximum transverse dimension of less than 13 millimeters. And the tampon undergoes a growth, upon fluid absorption, in transverse dimension of at least 7 millimeters.

In accordance with a second exemplary embodiment, there has now been provided a tampon comprising a mass of absorbent material which has been compressed into a generally cylindrical, self-sustaining form. The tampon has a syngyna absorbent capacity of between about 6 and about 9 grams. And the tampon has an average expansion rate of greater than 1.7 millimeters per minute after absorbing 3 grams of sheep's blood at a rate of about 1 gram per minute.

In accordance with a third exemplary embodiment, there has now been provided a tampon comprising a mass of absorbent material which has been compressed into a generally cylindrical, self-sustaining form. The tampon has a syngyna absorbent capacity of between about 6 and about 9 grams. And the tampon undergoes a growth, upon fluid absorption, in transverse dimension of greater than 13 millimeters in the absence of a contained pressure.

In accordance with a fourth exemplary embodiment, there has now been provided a tampon comprising a mass of absorbent material which has been compressed into a generally cylindrical, self-sustaining form. The tampon has a syngyna absorbent capacity of between about 9 and about 12 grams. Subsequent to compression, the generally cylindrical, self-sustaining form comprises a maximum transverse dimension of less than 14 millimeters. And the tampon undergoes a growth, upon fluid absorption, in transverse dimension of at least 7 millimeters while under a contained pressure of 0.25 psi.

In accordance with a fifth exemplary embodiment, there has now been provided a tampon comprising a mass of absorbent material which has been compressed into a generally cylindrical, self-sustaining form. The tampon has a syngyna absorbent capacity of between about 9 and about 12 grams. Subsequent to compression, the generally cylindrical, self-sustaining form comprises a maximum transverse dimension of 14 millimeters or less. And the tampon undergoes a growth, upon fluid absorption, in transverse dimension of greater than 10 millimeters while under a contained pressure of 0.25 psi.

In accordance with a sixth exemplary embodiment, there has now been provided a tampon comprising a mass of absorbent material which has been compressed into a generally cylindrical, self-sustaining form. The tampon has a syngyna absorbent capacity of between about 9 and about 12 grams. Subsequent to compression, the generally cylindrical, self-sustaining form comprises a maximum transverse dimension of 14 millimeters or less. And the tampon undergoes a growth, upon fluid absorption, in transverse dimension of greater than 15 millimeters in the absence of a contained pressure.

In accordance with a seventh exemplary embodiment, there has now been provided a tampon comprising a mass of absorbent material which has been compressed into a generally cylindrical, self-sustaining form. The tampon has a syngyna absorbent capacity of between about 9 and about 12 grams. And the tampon undergoes a growth, upon fluid absorption, in transverse dimension of greater than 15 millimeters in the absence of a contained pressure.

The present invention also relates to methods of making tampons. In accordance with one exemplary embodiment, there has now been provided a method comprising the steps of providing a mass of absorbent material; optionally disposing a liquid permeable overwrap over at least a portion of the absorbent material; compressing the mass of absorbent material into a generally cylindrical, self-sustaining form having a density of greater than 0.35 g/cc and a maximum transverse dimension of less than 13 millimeters; transferring the generally cylindrical, self-sustaining form into a carrier; delivering energy to the generally cylindrical, self-sustaining form to stabilize the same into a finished tampon; wherein the tampon has a syngyna absorbent capacity of between about 6 and about 9 grams; and wherein the tampon undergoes a growth, upon fluid absorption, in transverse dimension of at least 7 millimeters.

In accordance with a second exemplary embodiment, there has now been provided a method comprising the steps of providing a mass of absorbent material; optionally disposing a liquid permeable overwrap over at least a portion of the absorbent material; compressing the mass of absorbent material into a generally cylindrical, self-sustaining form having a density of greater than 0.35 g/cc and a maximum transverse dimension of less than 14 millimeters; transferring the generally cylindrical, self-sustaining form into a carrier; delivering energy to the generally cylindrical, self-sustaining form to stabilize the same into a finished tampon; wherein the tampon has a syngyna absorbent capacity of between about 9 and about 12 grams; and wherein the tampon undergoes a growth, upon fluid absorption, in transverse dimension of at least 7 millimeters.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION

Figure 1:
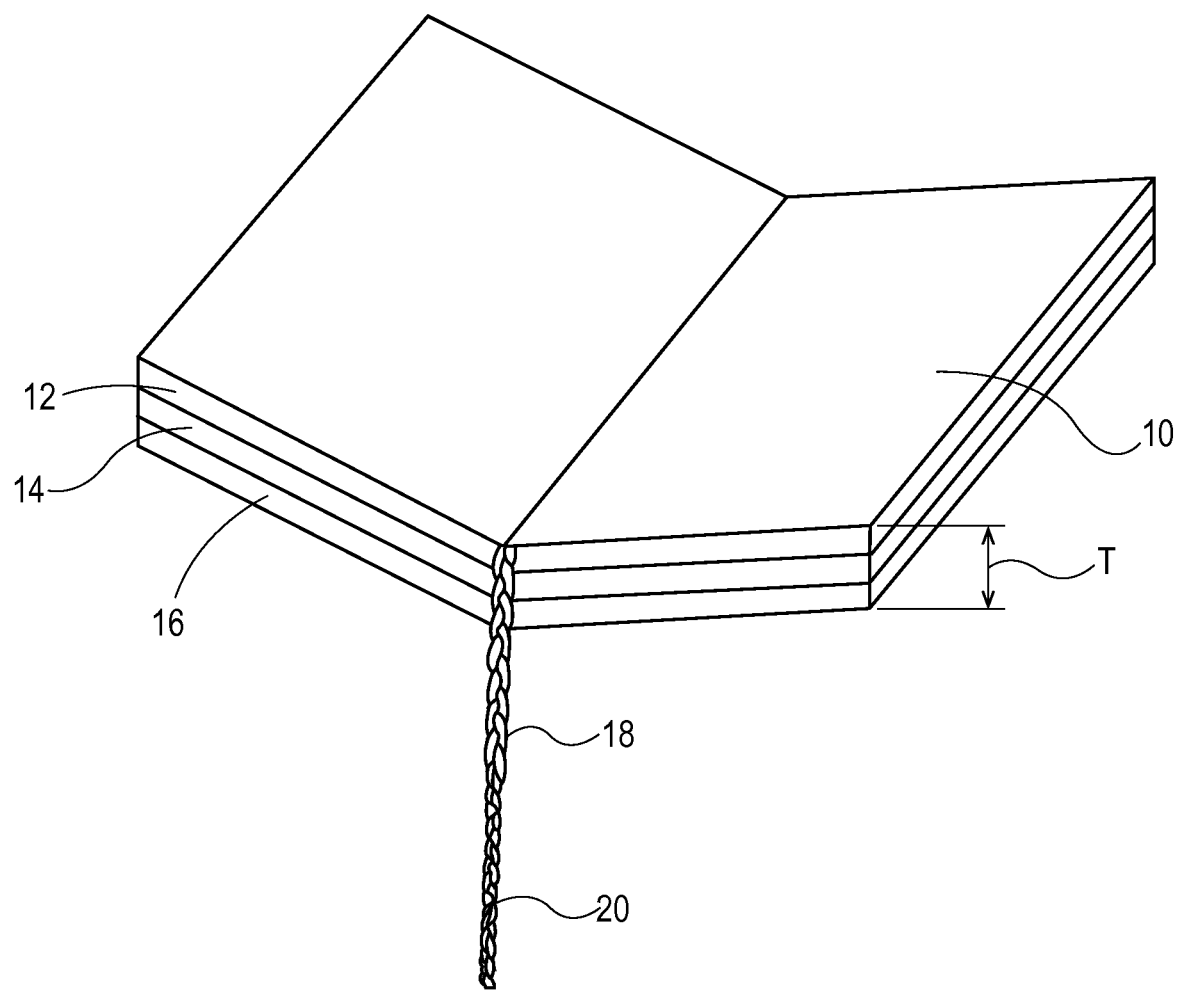
FIG. 1 is a perspective view of an exemplary tampon pledget of the present invention.

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein, the terms "pledget" and "tampon pledget" refer to a mass of absorbent material prior to compression of such material into tampon as described below. Tampon pledgets are sometimes referred to as a tampon blank, or a softwind.

As used herein, the term "tampon" refers to any type of absorbent structure which is inserted into the vaginal canal or other body cavities for the absorption of menses or other bodily exudates. Tampons typically are constructed from an absorbent material which has been compressed in any or all of the width direction, the radial direction, and the axial direction, in order to provide a tampon which is of a size and stability to allow insertion within the vagina or other body cavity. A tampon which has been so compressed is referred to herein as having a "self-sustaining" form. That is, the degree of compression and or conditioning of the absorbent material results in a tampon that will tend to retain its general shape and size prior to insertion into the body. The tampons of the present invention are "fluid-expanding" tampons that expand or uncompress upon contact and absorption of fluid. Fluid expanding tampons are contrasted to "mechanically expanding" tampons that may use springs or some other mechanical supplier of force to expand. An example of such a mechanically expanding tampon is described in U.S. Pat. No. 3,706,311 to Kohx et al.

The "syngyna" test is an industry standard tampon absorbency capacity test. The apparatus and method for performing this tampon absorbency test are provided in 21 United States Code of Federal Regulation 801.430. In the United States and other regions, tampons carry standardized absorbency labels according to syngyna test absorbency ranges. Tampons absorbing less than 6 grams of fluid are labeled "light absorbency," tampons absorbing 6 to 9 grams are labeled "regular absorbency," tampons absorbing 9 to 12 grams are labeled "super absorbency," tampons absorbing 12 to 15 grams are labeled "super plus absorbency," and tampons absorbing 15 to 18 grams are labeled "ultra absorbency."

Tampon expansion and expansion rates are calculated with the dynamic expansion test that includes a few variations from the standard syngyna test and that is described in greater detail towards the end of the instant specification in the Test Methods section.

Tampons of the present invention are formed from an uncompressed mass of absorbent material. The mass of absorbent material is generally in the form of one or more layers of fibrous materials. As noted above, the uncompressed mass of material is sometimes called a pledget or tampon blank. FIG. 1 shows an exemplary tampon pledget 10 comprising three layers of absorbent materials 12, 14, and 16 that combine to define a pledget thickness T; an optional secondary absorbent 18 in the form of a braid, and a withdrawal string 20. The skilled artisan should appreciate that the mass of absorbent material or pledget may be any suitable shaped, size, material, or construction. While pledget 10 is shown having a generally rectangular shape, other shapes are possible, including, for example, chevron, trapezoidal, triangular, semi-circular, "bow-tie", and H.

The pledget and tampon may be constructed from a wide variety of liquid-absorbing materials commonly used in absorbent articles such as, for example, rayon, cotton, or comminuted wood pulp which is generally referred to as airfelt. Examples of other suitable absorbent materials include creped cellulose wading; meltblown polymers including coform; chemically stiffened, modified or crosslinked cellulosic fibers; synthetic fibers such as crimped polyester fibers; foam; paper; superabsorbent materials; absorbent gelling materials or combinations of mixtures of these. Preferably, the absorbent materials include rayon, cotton, or a combination thereof. In one embodiment, 100% rayon is employed because rayon has a slightly higher absorbency per weight in comparison to cotton and therefore a smaller tampon can be produced on a fixed fiber weight basis.

The tampon pledget may be compressed or may be manipulated further prior to compression. For example, the mass of absorbent material may for example be rolled, folded, or otherwise altered in profile to help with compression and/or affect the expansion properties during use. A liquid permeable overwrap may also be placed over some or all of the mass of absorbent material prior to compression. A representative, non-limiting list of suitable overwrap materials includes rayon, cotton, bicomponent fibers, polyethylene fibers, polypropylene fibers, and polyethylene/polypropylene fiber mix.

The tampon pledget and optional overwrap are compressed into a generally cylindrical, self-sustaining form in the width direction, the radial direction, the axial direction, or any combination of these directions. Alternative compression directions can also be used. The pledgets can be compressed to a density ranging from about 0.3 to about 0.45 grams per cubic centimeter. The method for determining tampon density is provided below in the Test Methods section. In preferred embodiments, the pledgets are compressed to a density of greater than 0.35 grams per cubic centimeter, or a density of greater than 0.4 grams per cubic centimeter. For comparison, the assignee of the present invention currently manufactures TAMPAX brand tampons, wherein the regular and super absorbency versions have a density of around 0.33 grams per cubic centimeter.

Figure 2:
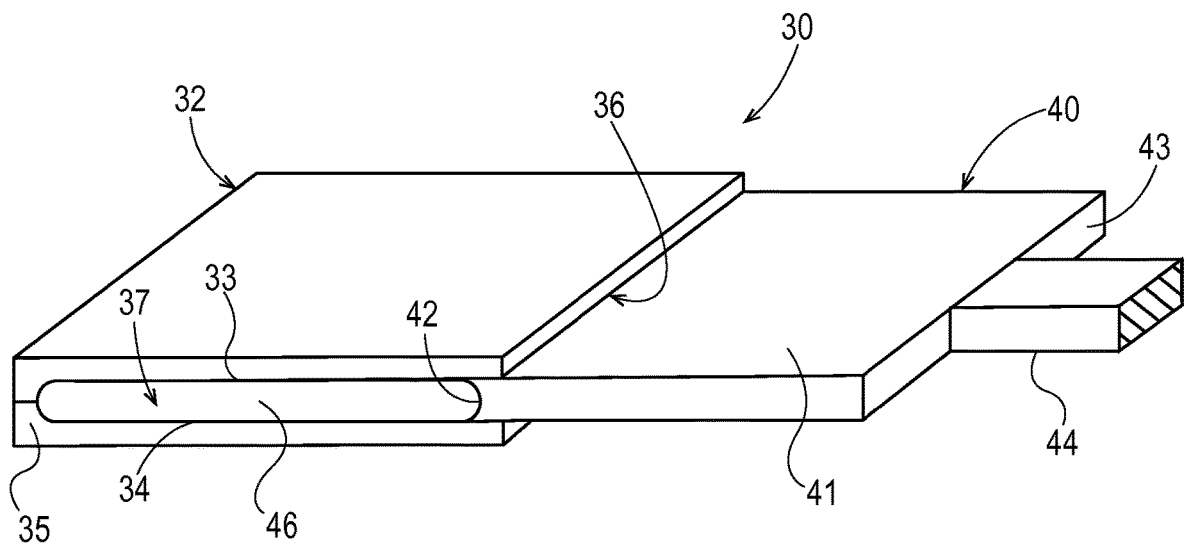
FIG. 2 is a perspective view of an exemplary tampon mold (in an open position) suitable for making tampons of the present invention.
Figure 3:
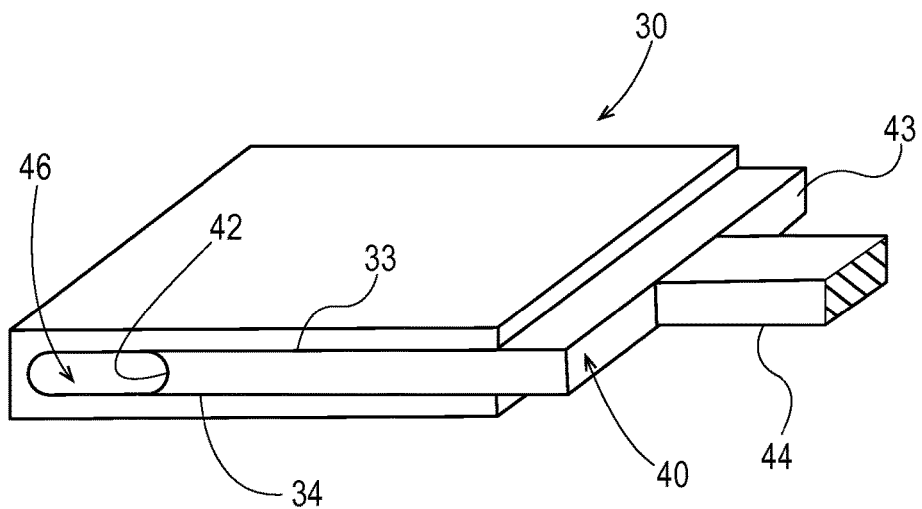
FIG. 3 is a perspective view of the mold shown in FIG. 2 in a closed position.

FIGS. 2 and 3 illustrate an exemplary tampon compression mold 30, with the mold in an open position in FIG. 2 and a closed position in FIG. 3. Exemplary mold 30 comprises a crossdie that includes a U-shaped anvil 32. The crossdie includes a top plate 33 and a juxtaposed bottom plate 34 extending from an end wall 35 connecting the top and bottom plates 33 and 34 to an open end 36 thereby forming a channel 37 between the top and bottom plates. The crossdie also includes a die or for application member 40 comprising a solid plate 41 extending from a leading end 42 to a trailing end 43 and an actuating rod 44 connected to trailing end 43 for reciprocating the die or force application member 40 within channel 37 of anvil 32. Leading end 42 of the die or force application member 40, the top and bottom plates 33 and 34, and the end wall 35 of the anvil 32 form a compression mold cavity 46 within the channel 37 for receiving uncompressed tampon pledgets.

Compression mold cavity 46 is shown having an oval cross-sectional shape, but it should be understood that it can have other shapes, such as, for example, round, square, polygonal, and rectangular cross-sectional shapes depending on the desired shape or cross-section of the formed tampon. It should also be understood that the compression mold cavity may have a varying or irregular width depending on the desired shape of the formed tampon along its length.

Figure 4:
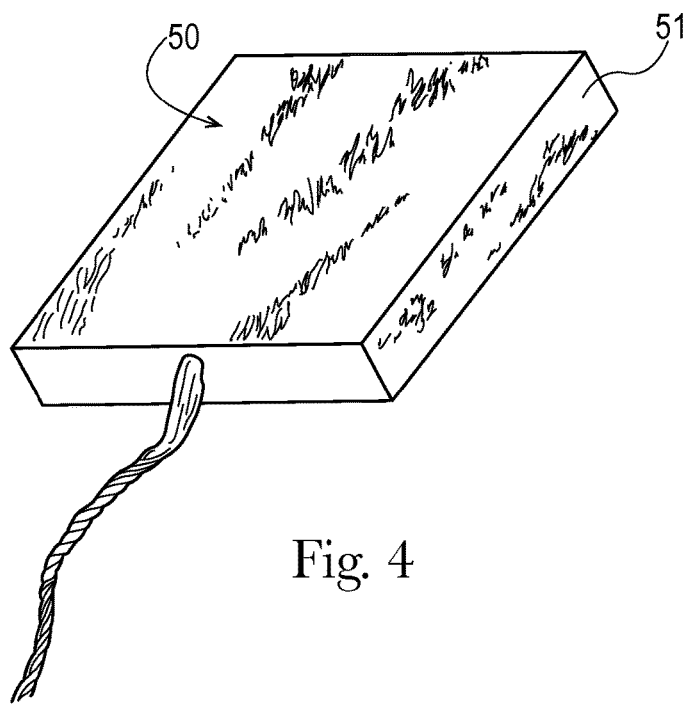
FIG. 4 is perspective view of another exemplary tampon pledget of the present invention.
Figure 5:
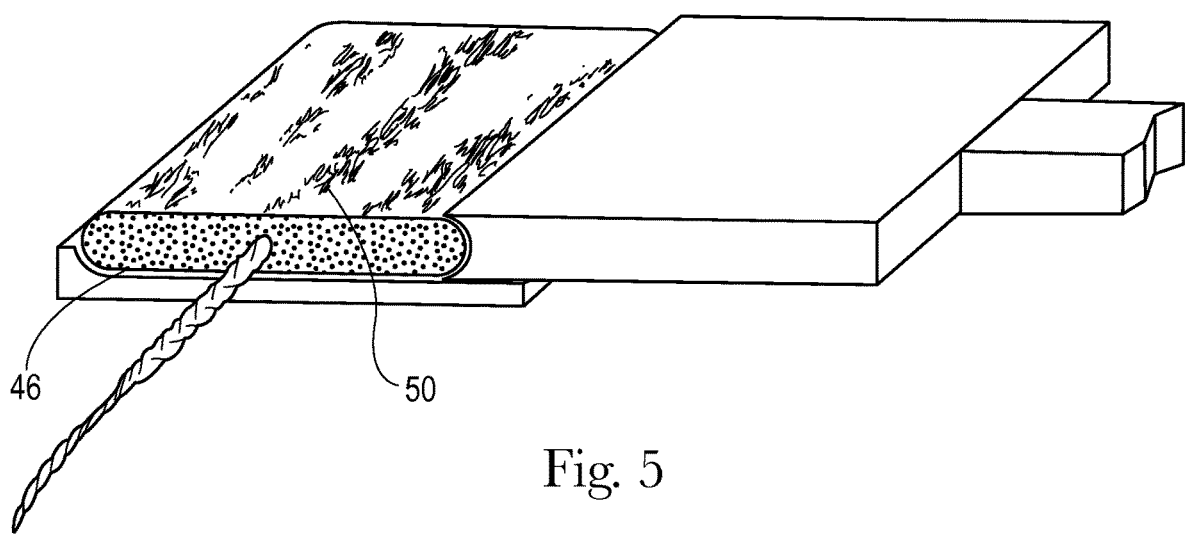
FIG. 5 is a perspective view of the tampon pledget shown in FIG. 4 as positioned within a mold cavity prior to compression of the pledget.
Figure 6:
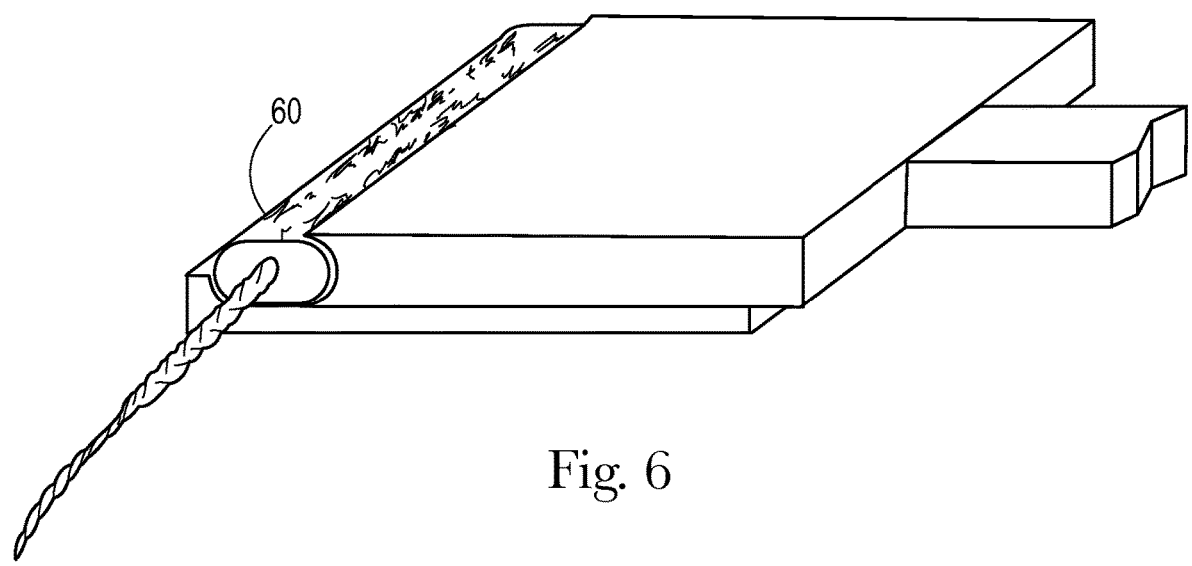
FIG. 6 is a perspective view of the tampon pledget in FIG. 5 after it has been compressed.

FIG. 4 shows another exemplary tampon pledget 50 that is constructed from a single layer of absorbent material 51. Pledget 50 is shown, in FIG. 5, placed in compression mold cavity 46. And FIG. 6 illustrates a compressed pledget 60 after it has been compressed in a widthwise direction. Compressed pledget 60 can then be compressed axially while transferring it to other aspects of a manufacturing line and/or to form a dome on the insertion end of the compressed pledget.

The skilled artisan should appreciate that the compression equipment and compression functions as shown in FIGS. 2 to 6 are exemplary in nature; and that other equipment and methods of compressing a pledget are contemplated by the present invention. The degree of compression of the uncompressed pledget 50 in the compression mold cavity 46 in the widthwise direction may be a major component of the compression. The degree of compression of the uncompressed pledget 50 in the thickness and lengthwise directions may be a minor component of the compression.

The compressed pledgets may optionally be conditioned or "set" to achieve a self-sustaining form. Conditioning generally involves imparting energy into the compressed pledget. Methods of setting or stabilizing the tampon size and shape include heating a compressed pledget with steam or thermal gradient conduction or microwaving as disclosed in U.S. Pat. No. 7,047,608. In certain embodiments, a heated gas or other medium can be applied to the compressed pledget 50 via at least one pore or fluid communication passage while the compressed pledget 50 is within the closed compression mold cavity 46. Preferably, the compressed pledget is subject to a conditioning via a microwave source for up to 25 seconds. The power of the microwave can be 5000-6000 Watts.

Figure 7:
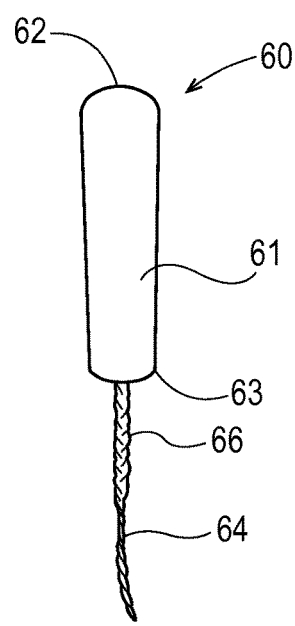
FIG. 7 is a side view of an exemplary tampon of the present invention.

FIG. 7 shows an exemplary tampon 60 having a generally cylindrical, self-sustaining form 61 that includes an insertion end 62 and a withdrawal end 63, a withdrawal string 64, and an optional secondary absorbent 66. Withdrawal strings useful in the present invention can be made of any suitable material known in the prior art, such as, e.g., cotton and rayon. The secondary absorbent is shown in FIGS. 1 and 7 to be in the form of a braid. Other secondary absorbent options are feasible including, but not limited to, those described in U.S. Pat. No. 6,258,075.

In certain embodiments, the tampons can be inserted digitally. When the tampons are intended to be digitally inserted, it can be desirable to provide a finger indent at the withdrawal end of the tampon to aid insertion and/or orientation, such as, for example, those described in U.S. Pat. No. 6,283,952. A tampon configured for digital insertion may also or alternatively comprise an overwrap material that extends beyond the withdrawal end of the tampon (see, for example, U.S. Pat. No. 6,840,927). Alternatively, the tampons can be inserted using an applicator; for example, tube and plunger type arrangements that can be plastic, paper, or other suitable material.

EXAMPLES

Regular absorbency tampons (syngyna absorbency of 6 to 9 grams) and super absorbency tampons (syngyna absorbency of 9 to 12 grams) according to the present invention were constructed with the properties shown in Table 1 below. The exemplary tampons were made from 100% rayon fiber pledgets at the listed basis weights and compressed primarily in the width direction with some axial compression during insertion end dome formation to a density above 0.4 grams per cubic centimeter. The apparatuses and methods described in U.S. Pat. No. 7,992,270 can be employed with the starting product attributes in Table 1 to make the exemplary tampons. Some of these tampons where then tested to determine their initial (that is, "dry" or prior to absorbing liquids) maximum transverse dimension (that is, "dry" or prior to absorbing liquids) and their expansion properties. The results are illustrated in Tables 2 and 3, along with the results of several commercially-available tampons and comparative tampons as described in commonly-owned U.S. Pat. Nos. 6,554,814 and 6,837,882.

TABLE 1

| Product Attribute | Invention Example 1 Regular Absorbency | Invention Example 2 Super Absorbency |
|---|---|---|
| Absorbent fiber | 100% rayon | 100% rayon |
| Pledget fiber loft | 6 mm | 7.9 mm |
| Fiber moisture | 12% | 12% |
| Fiber basis weight | 34 g/m | 52 g/m |
| Pledget length | 47.5 mm | 47.5 mm |
| Tampon length | 47.5 mm | 46.5 mm |
| Tampon maximum transverse dimension | 11.1 mm | 13.2 mm |
| Tampon density | 0.41 g/cm$^3$ | 0.41 g/cm$^3$ |
| Microwave power | 6000 W | 5900 W |
| Applicator diameter | 12 mm | 14 mm |

TABLE 2

| Regular absorbency (syngyna 6 to 9 grams) | Initial maximum transverse dimension (mm) | Growth with pressure (mm) | Growth without pressure (mm) | Expansion Rate (mm/minute) |
|---|---|---|---|---|
| Invention Example 1 | 11.5 | 9.5 | 14.9 | 1.89 |
| Playtex Gentle Glide | 12.5 | 4.5 | 5.7 | 1.03 |
| Playtex Sport | 12.1 | 6.5 | 5.8 | 1.63 |
| o.b. | 2.3 | 4.6 | 5.1 | 1.03 |
| Kotex Natural Balance | 15.5 | 4.5 | 5.8 | 0.91 |
| Kotex Sleek | 12.5 | 5.7 | 6.1 | 1.22 |
| Kotex Click | 12.1 | 4.0 | 6.1 | 0.93 |
| U.S. Pat. No. 6,554,814 | 13.0 | 9.0 | 12.0 | 1.64 |

TABLE 3

| Super absorbency (syngyna 9 to 12 grams) | Initial maximum transverse dimension (mm) | Growth with pressure (mm) | Growth without pressure (mm) | Expansion Rate (mm/minute) |
|---|---|---|---|---|
| Invention Example 2 | 13.8 | 11.5 | 15.9 | 1.87 |
| Playtex Gentle Glide | 14.2 | 6.0 | 7.7 | 1.13 |
| Playtex Sport | 14.1 | 6.6 | 7.2 | 1.41 |
| o.b. | 13.4 | 6.0 | 6.7 | 1.09 |
| Kotex Natural Balance | 18.9 | 4.0 | 4.4 | 0.51 |
| Kotex Sleek | 13.3 | 6.4 | 7.3 | 1.12 |
| Kotex Click | 14.0 | 6.4 | 6.8 | 1.10 |
| U.S. Pat. No. 6,837,882 | 14.0 | 10.0 | 15.0 | 1.90 |

Tables 2 and 3, above, include four parameters. The first parameter shown in the tables' second column is the initial maximum transverse dimension in their pre-insertion condition (for example, upon unwrapping a digital tampon or upon expulsion of the tampon from an applicator) and prior to the tampon absorbing liquids. This parameter is generally viewed or referenced as the "diameter" although some tampons due to their construction do not have a true circular cross section. The tampons are then tested according to the expansion test method described below. Expansion rates can be determined with this method and the fifth column of Tables 2 and 3 show the expansion rate at the point where the tampon has absorbed 3 grams of test fluid (defibrinated sheep's blood having a minimum 38% packed cell volume) at a test fluid delivery rate of 1 gram per minute. The third and fourth columns show the amount the tampon has expanded (tampon "growth") from its initial size to its size at the point of leakage in the test. The third column includes the tampon growth while pressure is still applied to the tampon to simulate expansion under normal usage with vaginal pressure is applied to the tampon. And the fourth column includes the total growth or expansion of the tampon when the pressure is removed from the tampon.

As can be seen in Table 2, the regular absorbency example provided by the present invention is the only tampon listed that has an initial maximum transverse dimension of less than 12 millimeters, but its expansion of 9.5 millimeters is the greatest in the list of products. The relatively small size can help improve ease and/or comfort of insertion and protection is not compromised due to the high level of expansion. The super absorbency example in Table 3 has a similarly impressive high level of expansion at 11.5 millimeters while under pressure—this is almost twice as much expansion as the comparative commercial products listed in the table.

Test Methods
Dynamic Expansion

Figure 8:
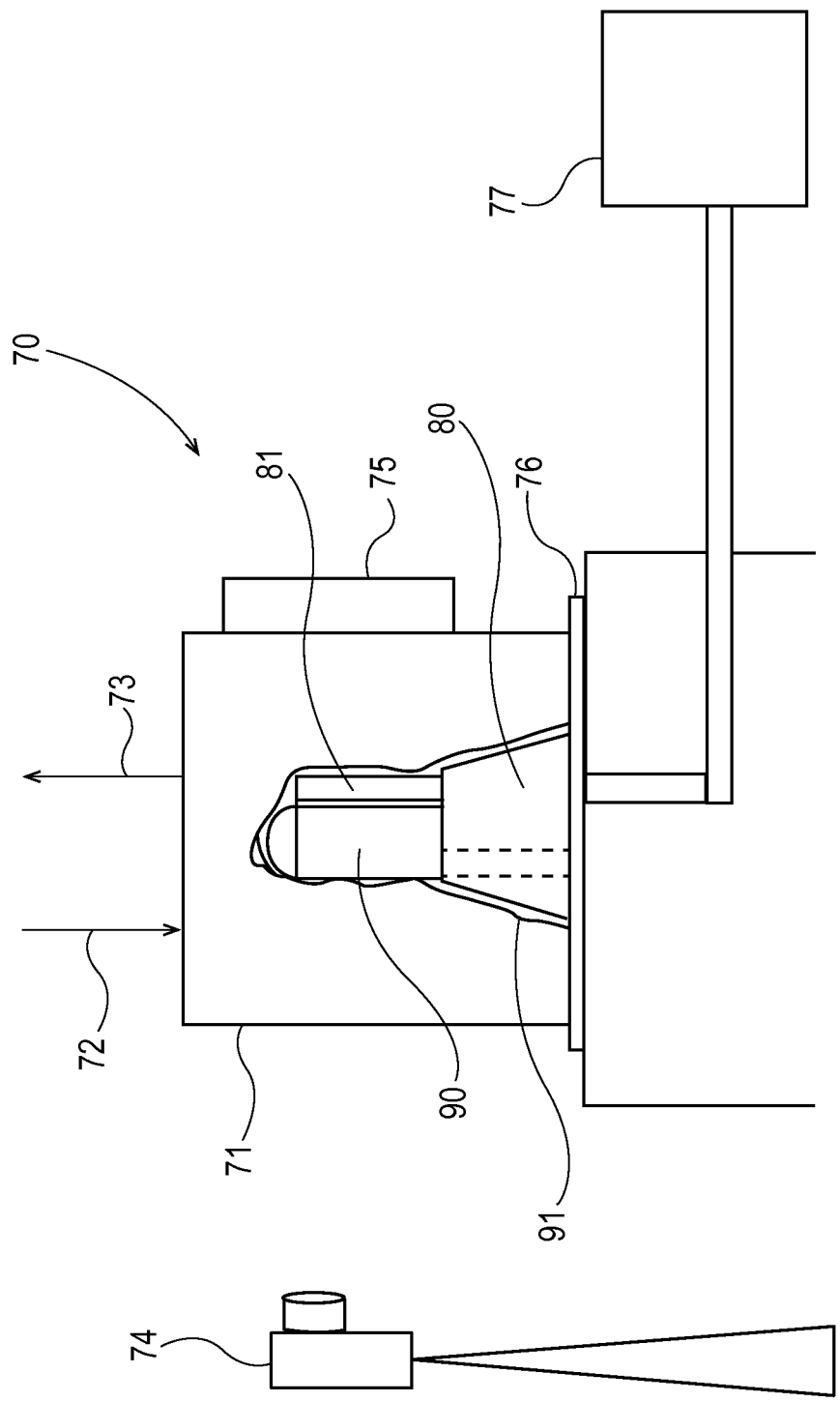
FIG. 8 is a schematic of an equipment assembly utilized in the dynamic expansion test method described herein.

FIG. 8 is a schematic of the assembly 70 utilized in the dynamic expansion test method described in detail below. Assembly 70 includes a pressure chamber 71, a pressurized air source 72, a manometer 73 for monitoring the pressure within pressure chamber 71, a camera 74, a light source 75, a silicone gasket 76, and a peristaltic pump 77 that delivers test fluid to a tampon. Within pressure chamber 71, there is a tampon mount 80 that includes test fluid delivery tube 81 and a drain hole 82 having a diameter of 3 millimeters. The test fluid delivery tube 81 has an opening that is 1.5 millimeters in diameter and that is 5 millimeters from the top of the tube for delivering test fluid to the side of the tampon. The test fluid delivery tube 81 is 48.5 millimeters in height and has a 9.5 millimeter diameter. A tampon 90 is mounted to test fluid delivery tube 81 and a condom 91 is placed over the tampon.

Purpose

This method provides a means of measuring the expansion of a tampon as it absorbs fluid while under pressure.

Equipment

Machine vision camera such as Cognex DVT 545 or equivalent

Light source appropriate for vision camera such as DVT Smart Light or equivalent Machine vision software such as DVT Frameworks or equivalent Tampon expansion chamber assembly (FIG. 1)

Air pressure regulator capable of delivering up to 2.0 psi

Sufficient tubing to deliver compressed air from regulator to assembly

Digital manometer capable of reading 0-2 psi such as a Meriam Meri-Cal Portable Digital Manometer Calibrator or equivalent Sufficient tubing to connect manometer to assembly Unlubricated latex condoms having a tensile strength of 17-30 MPa Peristaltic pump and appropriate tubing, capable of delivering 1.0+/−0.01 mL/minute Digital caliper gauge, readable to 0.01 mm Cylinders (4), each 55+/−0.1 mm long and of the following diameters: 12+/−0.02 mm, 16+/−0.03 mm, 20+/−0.04 mm, and 24+/−0.04 mm Balance, readable to 0.01 gram Timer or stopwatch, readable to 1 second Double-sided tape Beaker Magnetic stir plate Magnetic stir bars Test fluid: Defibrinated Sheep's Blood, minimum 38% packed cell volume, available at Cleveland Scientific Ltd. (Bath, Ohio)

Equipment Set-Up:
1. Refer to FIG. 8 for tampon expansion assembly schematic.
2. Position the camera so that when a tampon is mounted on the platform inside the assembly, nothing is obstructing the camera's view of the tampon, and so that the entire tampon (from tip to base) is visible in resulting image.
3. Position the light source opposite the camera to completely backlight the tampon from tip to base and side to side (the light source may be mounted to the tampon expansion chamber cover).
4. Connect compressed air source and manometer to the tampon expansion chamber using appropriate tubing.
5. Place appropriate tubing in peristaltic pump head. Connect one end of tubing to the tampon expansion assembly via the tube that extends from the underside of the tampon mount; place the other end of the tubing into a beaker containing test fluid at 23+/−3° C. (73+/−5° F.).
6. Continuously and moderately stir test fluid to avoid separation.
7. Configure vision system:
   a. Sensors are set at the midpoint of the tampon's length (50%), at approximately 28% of the tampon's length (from the top), and at approximately 67% of the tampon's length.
   b. Sensors find the edges of the tampon by determining a difference in grayscale.
   c. Sensors are approximately 2.08+/−0.2 mm in height
   d. Measurement data are collected every 5 seconds
8. Following the vision system's operating instructions, the system is calibrated using cylinders of known diameter to obtain a mm/pixel scale.

Equipment Verification:
1. The test fluid pump is set to deliver fluid at 1.00 (+/−0.01) gram/minute. This flow-rate is verified prior to testing. The test fluid delivery tube is left full of fluid between test specimens.
2. Place a cylinder on the tampon mount, close the tampon expansion chamber, and use the configured vision system to measure the maximum width of the cylinder. Compare this value to the caliper measurement of the cylinder; they should agree to within 7%. Repeat with other cylinders.

Sample Preparation:
1. Samples in their applicators and wrappers are equilibrated in the lab for at least 4 hours at 23+/−3° C. (73+/−5° F.) and 50+/−5% relative humidity prior to testing.
2. Samples are not removed from their wrappers or applicators until immediately prior to testing.
3. The withdrawal string of the tampon is removed. If a braid (e.g., that on TAMPAX PEARL tampons) or a skirt (e.g., that on TAMPAX compak) is present on the tampon, it is left intact.

Test Procedure:
1. Using the digital caliper gauge, measure the length and width of the dry tampon to the nearest 0.1 mm. The width is defined as the tampon's widest point along the length of the tampon. This is the tampon's width at time=0, or Tampon Dry Width.
2. Measure the dry weight of the tampon to the nearest 0.01 gram.
3. Place a small amount of tape on the fluid delivery tube.
4. Place the sample on the tampon mount in the expansion chamber. If the sample's construction is that of a compressed, flat, sewn pad, mount the tampon so that the sewn side (seam) is against the fluid delivery tube and adhered to the tape. If tampon is of differing construction, mount securely against fluid delivery tube.
5. Unroll a condom and place it over the tampon and the sample mount. The condom should fit loosely over the tampon, and there should be approximately 2 cm of space between the top of the condom and the top of the tampon.
6. Place the expansion chamber cover over the sample mount and clamp it down tightly against the silicone gasket, making an airtight seal with the base.
7. Turn on the air pressure and regulate to 0.25 psi. Confirm that the chamber is holding 0.25 psi with the manometer.
8. The condom should now be snug against the tampon.
9. Start the vision system and inspect the resulting image. If folds of the condom appear at sides or top of tampon in image, open chamber, readjust the condom, and repeat this step until the condom is smooth along the sides of the tampon in the image, e.g., no creases/wrinkles appear.
10. Once a clean image is obtained and the pressure is verified, simultaneously begin the vision system and the fluid delivery pump.
11. Continue pumping fluid into the tampon until it reaches the upper limit of its absorbency class. For example, stop the test for a Super tampon when fluid has been pumped for 12 minutes (the equivalent of 12 grams); a Regular for 9 minutes, etc. Once this time is reached, stop the vision system and fluid delivery pump at the same time.
12. Remove the tampon from the chamber.
13. Measure the wet weight of the tampon to the nearest 0.01 gram.
14. Using the digital caliper gauge, measure the length and width of the wet tampon to the nearest 0.1 mm. The width is defined as the tampon's widest point along the length of the tampon. This is the tampon's width at time=final, or Tampon Wet Width.
15. Collect the following data from the vision system: tampon width at the top, middle, and bottom, initially and at every 5 seconds of fluid loading. These are Tampon Width$_{[initial]}$ and Tampon Width$_{[at\ seconds]}$.
16. Calculate the following for each time point and sensor location:

Tampon Width(mm)=Dry Tampon Width(mm)+ (Tampon Width$_{[at\ seconds]}$(mm)−Tampon Width$_{[initial](mm)}$)

17. From all sensor data (top, middle, and bottom), determine the Maximum Tampon Width (mm) from the calculated data at 180 seconds.
18. From all sensor data (top, middle, and bottom), determine the Maximum Tampon Width (mm) from the calculated data overall (i.e. all time points). This is the Maximum Width Overall (mm).

19. Calculate the Maximum Width Growth (mm):

Maximum Width Growth(mm)=Maximum Width Overall(mm)−Dry Tampon Width(mm)

20. Calculate the Expansion Rate (mm/min):

Expansion Rate(mm/min)(Maximum Width$_{[at\ 180\ seconds]}$−Width$_{[Initial]}$)/3 minutes 21. Calculate the Expanded Growth, No Pressure:

Expanded Growth, No Pressure=Tampon Wet Width−Tampon Dry Width

Tampon Density

The following steps are followed to calculate the density of a tampon according to the present invention. The tampon withdrawal string (or comparable withdrawal structure) and any existing secondary absorbent feature (e.g., a braid) is cut at the bottom of the tampon absorbent body. The tampon body is then weighed to the nearest 0.01 grams. And the tampon body length is measured to the nearest 0.1 millimeters. The tampon body is then immerse into isopropyl alcohol for 30 seconds or until air bubbles stop. Remove the tampon from the alcohol and allow the excess alcohol to drip from the tampon for 15 seconds. Separately a test cylinder with spout is filled with isopropyl alcohol until it overflows at the spout into a 50 milliliter beaker. Tare the 50 milliliter beaker. Place the tampon body after the excess has dripped from the same slowly into the cylinder containing the standard volume of isopropyl alcohol. Collect the overflow of isopropyl alcohol from the spout that resulted from the addition of the tampon body. Obtain the weight of the isopropyl alcohol that overflowed the test cylinder to the nearest 0.01 grams.

Tampon volume(milliliters)=weight of overflowed alcohol/0.780 grams per milliliter Tampon density(grams per milliliter)=tampon weight (grams)/tampon volume The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 millimeters" is intended to mean "about 40 millimeters."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent tampon comprising a mass of absorbent material which has been compressed into a generally cylindrical, self-sustaining form in a transverse dimension and in a longitudinal dimension, wherein subsequent to compression the generally cylindrical, self-sustaining form comprises a maximum transverse dimension of less than 13 millimeters, wherein the tampon has a syngyna absorbent capacity of between about 6 and about 9 grams, and wherein the tampon undergoes a growth, upon fluid absorption, in the transverse dimension of at least 7 millimeters according to the dynamic expansion test, and in the longitudinal dimension.

2. The tampon of claim 1, wherein the tampon undergoes a growth, upon fluid absorption, in transverse dimension of greater than 9.0 millimeters while under a contained pressure of 0.25 pounds per square inch.

3. The tampon of claim 1, wherein the tampon undergoes a growth, upon fluid absorption, in transverse dimension of greater than 13 millimeters in the absence of a contained pressure.

4. The tampon of claim 1, wherein the mass of absorbent material comprises 100% of rayon.

5. The tampon of claim 4, wherein the generally cylindrical, self-sustaining form has a density of greater than 0.35 grams per cubic centimeter.

6. The tampon of claim 1, wherein the generally cylindrical, self-sustaining form has a density of greater than 0.40 grams per cubic centimeter.

7. The tampon of claim 1, wherein subsequent to compression the generally cylindrical, self-sustaining form comprises a maximum transverse dimension of less than 12 millimeters.

8. An absorbent tampon comprising a mass of absorbent material which has been compressed into a generally cylindrical, self-sustaining form in a transverse dimension and in a longitudinal dimension, wherein subsequent to compression the generally cylindrical, self-sustaining form comprises a maximum transverse dimension of less than 13 millimeters, wherein the tampon has a syngyna absorbent capacity of between about 6 and about 9 grams, and wherein the tampon has an average expansion rate in the transverse dimension of greater than 1.7 millimeters per minute after absorbing 3 grams of sheep's blood at a rate of about 1 gram per minute according to the dynamic expansion test, and wherein the tampon undergoes growth, upon fluid absorption, in the longitudinal dimension.

9. The tampon of claim 8, wherein the tampon undergoes a growth, upon fluid absorption, in transverse dimension of greater than 9.0 millimeters while under a contained pressure of 0.25 pounds per square inch.

10. The tampon of claim 8, wherein the tampon undergoes a growth, upon fluid absorption, in transverse dimension of greater than 13 millimeters in the absence of a contained pressure.

11. The tampon of claim 8, wherein the mass of absorbent material comprises 100% of rayon.

12. The tampon of claim 11, wherein the generally cylindrical, self-sustaining form has a density of greater than 0.35 grams per cubic centimeter.

13. An absorbent tampon comprising a mass of absorbent material which has been compressed into a generally cylindrical, self-sustaining form in a transverse dimension and in a longitudinal dimension, wherein subsequent to compression the generally cylindrical, self-sustaining form comprises a maximum transverse dimension of less than 14 millimeters, wherein the tampon has a syngyna absorbent capacity of between about 9 and about 12 grams, and wherein the tampon undergoes a growth, upon fluid absorption, in the transverse dimension of at least 7 millimeters while under a contained pressure of 0.25 psi according to the dynamic expansion test and in the longitudinal dimension.

14. The tampon of claim 13, wherein the mass of absorbent material comprises 100% of rayon.

15. The tampon of claim 14, wherein the generally cylindrical, self-sustaining form has a density of greater than 0.35 grams per cubic centimeter.

16. The tampon of claim 13, wherein the generally cylindrical, self-sustaining form has a density of greater than 0.40 grams per cubic centimeter.

17. The tampon of claim 13, wherein the tampon undergoes a growth, upon fluid absorption, in transverse dimension of greater than 10.0 millimeters while under a contained pressure of 0.25 psi.

* * * * *